US012628855B2

(12) United States Patent
Chamberland et al.

(10) Patent No.: US 12,628,855 B2
(45) Date of Patent: May 19, 2026

(54) CANNABIS PLANT RESIDUE AND USE THEREOF

(71) Applicant: Panag Pharma Inc., Halifax (CA)

(72) Inventors: Guy Chamberland, Boucherville (CA); Randy Albert Ringuette, Ottawa (CA); Melanie Edna Mary Kelly, Halifax (CA); Jacqueline Jacques, San Juan Capistrano, CA (US); Benjamin Matthew Allain, Halifax (CA)

(73) Assignee: Altheda Wellness Innovation Inc., Halifax (CA)

( * ) Notice: Subject to any disclaimer, the term of this patent is extended or adjusted under 35 U.S.C. 154(b) by 428 days.

(21) Appl. No.: 18/014,290

(22) PCT Filed: Jun. 28, 2021

(86) PCT No.: PCT/CA2021/050886
§ 371 (c)(1),
(2) Date: Jan. 3, 2023

(87) PCT Pub. No.: WO2022/000077
PCT Pub. Date: Jan. 6, 2022

(65) Prior Publication Data
US 2023/0248040 A1    Aug. 10, 2023

Related U.S. Application Data

(60) Provisional application No. 63/046,915, filed on Jul. 1, 2020.

(51) Int. Cl.
*A23L 33/105*    (2016.01)
*A23L 33/135*    (2016.01)
*A23L 33/21*    (2016.01)
*A61K 36/185*    (2006.01)

(52) U.S. Cl.
CPC ........... *A23L 33/105* (2016.08); *A23L 33/135* (2016.08); *A23L 33/21* (2016.08); *A61K 36/3482* (2024.05)

(58) Field of Classification Search
CPC ...... A23L 33/105; A23L 33/21; A23L 33/135; A23L 33/22; A61K 2236/00
See application file for complete search history.

(56) References Cited

U.S. PATENT DOCUMENTS

2004/0048356 A1 *  3/2004  Johansson ................. A61P 3/06
435/252.3

FOREIGN PATENT DOCUMENTS

CN    100998414 A  *  7/2007

OTHER PUBLICATIONS

El-Sohaimy, "Nutritional Quality, Chemical, and Functional Characteristics of Hemp (*Cannabis sativa* ssp. *sativa*) Protein Isolate", Plants, 2022, 11, 2825, pp. 1-13 (Year: 2022).*

(Continued)

*Primary Examiner* — Changqing Li
(74) *Attorney, Agent, or Firm* — Borden Ladner Gervais LLP; Michael Damiani

(57) ABSTRACT

The present disclosure relates to a *cannabis* plant residue and its use as a prebiotic. The present disclosure also relates to a prebiotic composition comprising a *cannabis* plant residue and hempseed hull, and its use as a prebiotic. The present disclosure further relates to methods of providing a prebiotic comprising administering a *cannabis* plant residue of the present disclosure.

23 Claims, 2 Drawing Sheets

(56)         References Cited

OTHER PUBLICATIONS

Tufarelli, "Hemp seed (*Cannabis sativa* L.) cake as sustainable dietary additive in slow-growing broilers: effects on performance, meat quality, oxidative stability and gut health", Veterinary Quarterly, 2023, 43(1), pp. 1-12 (Year: 2023).*

CEN Standard Method EN 15662: Food of Plant Origin—Determination of Pesticide Residues Using GC-MS and/or LC-MS/MS Following Acetonitrile Extraction/partitioning and Clean-up by Dispersive SPE—QUEChERS method.—EP Chapter 2.8.13 Pesticide Residues, The European Pharmacopoeia, pp. 274-275.

Cheese and Cheese Products: Official Methods of Analysis of AOAC International, AOAC International, Gaithersburg, MD, USA 2005, 18th Edition, Official Method 933.05. (Modified), 25 Pages.

Dumas method (DGEN_S) Official Methods of Analysis of Aoac International, Aoac International, Gaithersburg, MD, USA, 2005, 18th Edition, Methods 968.06 and 992.15, (Modified).

Egg, Egg Products, and Mayonnaise: Official Methods of Analysis of AOAC International, Aoac International, Gaithersburg, MD, USA, 2005, 18th Edition, Official Method 925.32. (Modified).

Food Products that are not Dairy, Egg or Cheese Products: Official Methods of Analysis of AOAC International, AOAC, International, Gaithersburg, MD, USA, 2005, 18TH Edition, Official Methods 922.06 and 954.02. (Modified).

Gaisawat et al., "Probiotic Supplementation Is Associated with Increased Antioxidant Capacity and Copper Chelation in C. Difficile-infected Fecal Water," Nutrients, 2019, vol. 11(9), pp. 1-14.

German Research Association (DFG), Manual of Pesticide Residue Analysis, 1987, Volume I by Verlag Chemie, ISBN 3-527-27010-8, pp. 1-361.

Grigoryvev et al., "Hempseeds (Cannabis Spp.) As a Source of Functional Food Ingredients, Prebiotics and Phytosterols," Agricultural and Food Science, 2020, vol. 29, pp. 460-470.

Hayama et al., "Simple and Rapid Method for the Determination of Ethylenebisdithiocarbamate Fungicides in Fruits and Vegetables Using Liquid Chromatography with Tandem Mass Spectrometry," Analytical and Bioanalytical Chemistry, 2008, vol. 392, pp. 969-976.

Hepperle et al., "Analysis of Amitraz (Sum)" in Pears with Incurred Residues—Comparison of the Approach Covering the Individual Metabolites via Lc-ms/ms with the Approach Involving Cleavage to Dimethylaniline, Food Chemistry, 2015, vol. 166, pp. 240-247.

Lehotay, "Determination of Pesticide Residues in Foods by Acetonitrile Extraction and Partitioning with Magnesium Sulfate: Collaborative Study," Journal of AOAC International, 2007, vol. 90(2), pp. 485-520.

M100_T100 (M100T100_S) Official Methods of Analysis of AOAC International, AOAC International, Gaithersburg, MD, USA, 2005, 18th Edition, Methods 925.09 and 926.08, (Modified).

Ma et al., "Quality Specifications for Articles of Botanical Origin from the United States Pharmacopeia," Phytomedicine, 2018, pp. 1-38.

Merrill., et al., United States Department of Agriculture, "Energy Value of Foods", Agriculture Handbook No. 74, 1973, pp. 1-105.

Miranda et al., "The Impact of in Vitro Digestion on Bioaccessibility of Polyphenols from Potatoes and Sweet Potatoes and Their Influence on Iron Absorption by Human Intestinal Cells," Food & Function, 2013, vol. 4(11), pp. 1595-1601.

"Official Methods of Analysis of AOAC International," AOAC International, Gaithersburg, MD, USA, 2005, 18th Edition, Method 923.03., (Modified) 26 Pages.

Official Methods of Analysis of Aoac International, AOAC International, Gaithersburg, MD, USA, 2005, 18th Edition, Method 991.43, (Modified).

Stijve, "Gas Chromatographic Determination of Inorganic Bromide Residues—a Simplified Procedure," German Food Review, 1981, vol. 77(3) pp. 99-101.

Tzounis et al., "Flavanol Monomer-induced Changes to the Human Faecal Microflora," The British Journal of Nutrition, 2008, vol. 99(4), pp. 782-792.

* cited by examiner

CANNABIS PLANT RESIDUE AND USE THEREOF

CROSS-REFERENCE TO RELATED APPLICATIONS

The present disclosure is a 35 USC 371 national stage entry of PCT/CA2021/050886 filed on Jun. 28, 2021 and which claims the benefit of U.S. Provisional Patent Application No. 63/046,915, filed Jul. 1, 2020, the contents of which are incorporated herein by reference in their entirety.

FIELD

The present disclosure relates to *cannabis* plant residues and uses thereof as prebiotic supplements. The present disclosure also relates to methods of providing a prebiotic supplement to subject in need thereof.

INTRODUCTION

Human gastrointestinal tract is inhabited by various types of microorganisms that are important to human health. They assist digestion and suppress pathogens. An imbalance in gut microbial culture can lead to serious health conditions such as irritable bowel syndrome, colitis, Crohn's disease, cardiovascular conditions, and obesity. A growing body of research shows that gut microbiota is linked to general health in aging, to mental and emotional health, and to the central nervous system in general. The microbial population, or microbiota, relies on human diet as a source of energy. Its composition is influenced by the content of human diet. Certain non-digestible dietary substances including carbohydrates are known to be beneficial to intestinal microbes. These dietary substances or prebiotics are non-digestible to human digestive system, but can provide energy to the intestinal microbial inhabitants. Intestinal microorganisms can degrade prebiotics by for example fermentation. Sometimes, the prebiotic degradation product by one type of microorganism can serve as a prebiotic for another type of microorganism. It has also been shown that prebiotic degradation products can enter blood circulation and have beneficial effects on distant organs and systems. Prebiotics in general are known to be beneficial for the immune system function, glycemic control, cardiovascular system and GI health, and for the treatment and prevention of diabetes, obesity, osteoporosis and liver disease.

Normal human diet contains limited sources of prebiotics. However, the concentration of prebiotics in an average food intake is often insufficient. There exists a need to develop alternative prebiotic sources.

SUMMARY

It has been shown that the *cannabis* plant residue of the present disclosure can increase the growth of beneficial gut microbes including at least Lactobaccillus *rhamnosus* and *Bifidobacterium longum*. Accordingly, the *cannabis* plant residue of the present disclosure is useful as a prebiotic.

Further, it has been shown that hempseed hull can be mixed with the *cannabis* plant residue of the present disclosure and the resulting mixture can be used as a prebiotic. Accordingly, the composition comprising the *cannabis* plant residue of the present disclosure and hempseed hull can be useful as a prebiotic.

Accordingly, in one aspect, the present disclosure includes a *cannabis* plant residue.

In another aspect, the present disclosure includes a *cannabis* plant residue for use as a prebiotic dietary supplement.

In another aspect, the present disclosure includes a use of a *cannabis* plant residue in the preparation of a prebiotic dietary supplement.

In another aspect, the present disclosure includes a use of a *cannabis* plant residue as a prebiotic dietary supplement in a subject in need thereof.

In another aspect, the present disclosure includes a method of providing a prebiotic supplement to a subject in need thereof comprising administering to the subject an effective amount of a *cannabis* plant residue.

In some embodiments, the *cannabis* plant residue has a cannabinoid content of at most 5%. In some embodiments, the *cannabis* plant residue has a cannabinoid content of about 5% or less than 5%.

In some embodiments, the *cannabis* plant residue is obtained by removing at least 95%, 96%, 97, 98%, or 99% of cannabinoids from a *cannabis* plant.

In another aspect, the present disclosure includes a prebiotic composition comprising a *cannabis* plant residue and hempseed hull, the composition having a cannabinoid content of about 5% or less than 5%.

In another aspect, the present disclosure includes a method of providing a prebiotic supplement to a subject in need thereof comprising administering to the subject an effective amount of prebiotic composition of the present disclosure.

In another aspect, the present disclosure includes a use of a prebiotic composition of the present disclosure in the preparation of a prebiotic dietary supplement.

In another aspect, the present disclosure includes a use of a prebiotic composition of the present disclosure as a prebiotic dietary supplement in a subject in need thereof.

In another aspect, the present disclosure includes a prebiotic of the present disclosure for use as a prebiotic dietary supplement.

DRAWINGS

The embodiments of the disclosure will now be described in greater detail with reference to the attached drawings in which.

Figure 1:
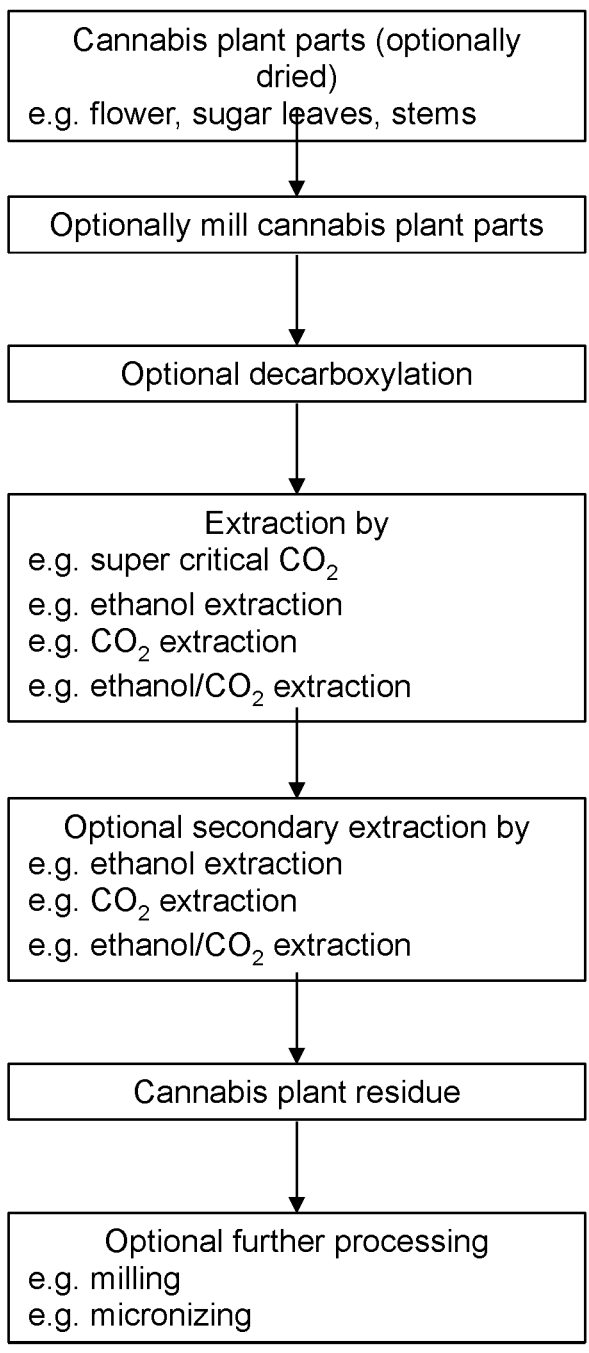
FIG. 1 shows a flowchart of an example of a treatment process to obtain the *cannabis* plant residue of the present disclosure.

Other features and advantages of the present disclosure will become apparent from the following detailed description. It should be understood, however, that the detailed description and the specific examples, while indicating embodiments of the disclosure, are given by way of illustration only and the scope of the claims should not be limited by these embodiments, but should be given the broadest interpretation consistent with the description as a whole.

DESCRIPTION OF VARIOUS EMBODIMENTS

I. Definitions

Unless otherwise indicated, the definitions and embodiments described in this and other sections are intended to be applicable to all embodiments and aspects of the present disclosure herein described for which they are suitable as would be understood by a person skilled in the art.

The term "and/or" as used herein means that the listed items are present, or used, individually or in combination. In effect, this term means that "at least one of" or "one or more" of the listed items is used or present. The term "and/or" with respect to pharmaceutically acceptable salts and/or solvates thereof means that the compounds of the disclosure exist as individual salts and hydrates, as well as a combination of, for example, a solvate of a salt of a compound of the disclosure.

As used in the present disclosure, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

As used in this disclosure and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The term "subject" as used herein includes all members of the animal kingdom including mammals, and suitably refers to humans. Thus, the methods and uses of the present disclosure are applicable to both human therapy and veterinary applications.

The term "pharmaceutically acceptable" means compatible with the treatment of subjects.

The term "cannabinoid" as used herein refers to C21 or C22 terpenophenolic compounds, their carboxylic acids, analogs and transformation products, and endo- and artificial compounds that bind to cannabinoid receptors. For example, when the cannabinoid naturally occurs in a plant such as *Cannabis sativa* plant, the cannabinoid is understood to be a phytocannabinoid.

The term "*cannabis* plant" as used herein refers to a plant of the species *Cannabis sativa*.

II. *Cannabis* Plant Residue and Prebiotic Composition of the Present Disclosure In one aspect, the present disclosure relates to a *cannabis* plant residue.

The *cannabis* plant residue of the present disclosure is prepared by removing cannabinoids from a *cannabis* plant that has a non-negligible level of cannabinoids. In some embodiments, the *cannabis* plant residue has a cannabinoid content of at most 5%. In some embodiments, the *cannabis* plant residue has a cannabinoid content of at most 3%, at most 1%, or at most 0.5%. In some embodiments, the *cannabis* plant residue has a cannabinoid content of at most 0.5% or 0.1%. In some embodiments, the *cannabis* plant residue has a cannabinoid content of about 5% or less than 5%. In some embodiments, the *cannabis* plant residue has a cannabinoid content of about 3% or less than 3%, about 1% or less than 1%, about 0.5% or less than 0.5%. In some embodiments, the *cannabis* plant residue is substantially free of cannabinoids.

In some embodiments, the *cannabis* plant residue is obtained by removing at least 95%, 96%, 97, 98%, or 99% of cannabinoids from a *cannabis* plant. For example, the *cannabis* plant residue is obtained by removing about 95%, about 96%, about 97%, about 98% or about 99% of cannabinoid from a *cannabis* plant. For example, the *cannabis* plant residue is obtained by removing at least 99.5%, 99.7%, 99.8% or 99.9% of cannabinoids from the *cannabis* plant. For example, the *cannabis* plant residue is obtained by removing about 99.5%, 99.7%, 99.8% or 99.9% of cannabinoid from the *cannabis* plant.

In some embodiments, the *cannabis* plant residue is obtained by a treatment process comprising removing cannabinoids from a *cannabis* plant. In some embodiments, the removing of cannabinoids from the *cannabis* plant is by super critical $CO_2$ extraction, by ethanol extraction, by $CO_2$ extraction, and/or by ethanol/$CO_2$ extraction. In some embodiments, the removing of cannabinoids from the *cannabis* plant is by super critical $CO_2$ extraction and ethanol extraction. In some embodiments, the removing of cannabinoids from the *cannabis* plant is by super critical $CO_2$ extraction followed by a secondary ethanol extraction.

In some embodiments, the *cannabis* plant comprises one or more dried *cannabis* plant parts selected from flower, sugar leaves and stems. For example, the *cannabis* plant comprises any part of the plant that is above ground.

In some embodiments, the treatment process further comprises milling the *cannabis* plant.

In some embodiments, the treatment process further comprises decarboxylating the *cannabis* plant.

In some embodiments, the super critical $CO_2$ extraction or the ethanol extraction is performed at a temperature of about 30° C. to about 90° C.

In some embodiments, the super critical $CO_2$ extraction or the ethanol extraction is performed at a pressure of about 1500 PSI to about 5000 PSI.

In some embodiments, the treatment process does not comprise fermentation of the *cannabis* plant.

In some embodiments, the *cannabis* plant residue is micronized. In some embodiments, the *cannabis* plant residue is not micronized. It is appreciated by a person skilled in the art that micronization can be performed with any suitable technique in the art. For example, jet micronization can be used. Micronized *cannabis* plant residue can have an average particle size of about 1 micron to about 10 microns.

In some embodiments, the *cannabis* plant residue comprises about 15% w/w to about 85% w/w of total dietary fiber. In some embodiments, the *cannabis* plant residue comprises about 20% w/w to about 80% w/w of total dietary fiber. In some embodiments, the *cannabis* plant residue comprises about 60% w/w to about 70% w/w of total dietary fiber.

In some embodiments, the *cannabis* plant residue comprises about 10% w/w to about 80% w/w of insoluble dietary fiber. In some embodiments, the *cannabis* plant residue comprises about 55% w/w to about 75% w/w of insoluble dietary fiber. In some embodiments, the *cannabis* plant residue comprises about 65% w/w of insoluble dietary fiber.

In some embodiments, the *cannabis* plant residue comprises about 0.5% w/w to about 60% w/w of carbohydrate. In some embodiments, the *cannabis* plant residue comprises about 1% w/w to about 3% w/w of carbohydrate. In some embodiments, the *cannabis* plant residue comprises about 2.5% w/w of carbohydrate.

In some embodiments, the *cannabis* plant residue comprises about 10% w/w to about 30% w/w of protein. In some embodiments, the *cannabis* plant residue comprises about 15% w/w to about 22% w/w of protein. In some embodiments, the *cannabis* plant residue comprises about 18% w/w of protein.

In another aspect, the present disclosure includes the *cannabis* plant residue of the present disclosure for use as a prebiotic dietary supplement.

In some embodiments, the *cannabis* plant residue is formulated for use in a unit dose of about 0.1 g to about 1.5 g. In some embodiments, the *cannabis* plant residue is formulated for use in the unit dose of about 0.3 g to about 1 g. In some embodiments, the *cannabis* plant residue is formulated for use in the unit dose of about 0.5 g to about 0.7 g. In some embodiments, the *cannabis* plant residue is formulated for use in the unit dose of about 0.5 g.

In some embodiments, the *cannabis* plant residue is used 2 or 3 times per day. In some embodiments, the *cannabis* plant residue is used 3 times per day.

In some embodiments, the *cannabis* plant residue is formulated for use in an amount of about 0.5 g to about 50 g per day, about 1 g to about 40 g per day, or about 10 g to about 30 g per day. In some embodiments, the *cannabis* plant residue is formulated for use in the amount of about 0.5 g to about 3 g per day. In some embodiments, the *cannabis* plant residue is formulated for use in the amount of about 1.5 g to about 3 g per day. In some embodiments, the *cannabis* plant residue is formulated for use in the amount of about 1.5 g per day. In some embodiments, the *cannabis* plant residue is formulated for use in an amount of at least 1.5 g per day.

In some embodiments, the *cannabis* plant residue is used in combination with a probiotic supplement, a parabiotic supplement, a postbiotic supplement, a second prebiotic supplement, and/or one or more cannabinoids.

In some embodiments, the second prebiotic supplement is selected from hempseed hull, fructans, galacto-oligosaccharides, starch and/or glucose-derived oligosaccharides, pectin oligosaccharides, non-carbohydrate oligosaccharides, and combinations thereof. In some embodiments, the second prebiotic is selected from inulin, hempseed hull and combinations thereof. In some embodiments, the second prebiotic is hempseed hull. In some embodiments, the second prebiotic supplement is inulin.

In some embodiments, the probiotic supplement is microorganisms selected from *Lactobacillus* species, *Bifidobacterium* species, Baccilus species, *Streptococcus* species, *Enterococcus* species, *Saccharomyces* species, and combinations thereof.

In some embodiments, the second prebiotic supplement is inulin, and the inulin is formulated for use in a unit dose of about 1 g to about 3 g, about 1.5 g to about 2.5 g, or about 2 g. In some embodiments, the second prebiotic supplement is inulin, and the inulin is used in an amount of about 2 g to about 10 g per day, about 5 g to about 8 g per day, about 6 g to about 7 g per day, or about 6 g per day.

In some embodiments, the second prebiotic is hempseed hull. For example, the hempseed hull used in combination with the *cannabis* plant residue of the presentation disclosure can be particularly suitable for use as a prebiotic. For example, the hempseed hull of the present disclosure can have a high content of carbohydrate. For instance, the carbohydrate of the hempseed hull of the present disclosure can comprise predominantly polysaccharides including pectin, cellulose and/or xylan. In some embodiments, the hempseed hull of the present disclosure comprises about 45 wt %, about 50 wt %, about 55 wt %, about 60 wt %, about 62 wt %, or about 65 wt % of carbohydrate. In some embodiments, the hempseed hull comprises above 40 wt %, above 50 wt %, above 55 wt %, or above 60 wt % of carbohydrate. In some embodiments, the hempseed hull of the present disclosure comprises about 45 wt % to about 70 wt %, about 50 wt % to about 70 wt %, about 55 wt % to about 68 wt %, about 45 wt % to about 55 wt %, about 50 wt % to about 65 wt % of carbohydrate.

In some embodiments, *cannabis* plant residue is formulated for oral use.

In some embodiments, the *cannabis* plant residue is used contemporaneously with, prior to or subsequent to food in-take.

In some embodiments, the *cannabis* plant residue is formulated for use in a tablet, a capsule, a powder or a soft chewable tablet.

In some embodiments, the *cannabis* plant residue of the disclosure is orally administered, for example, with an inert diluent or with an assimilable edible carrier, or it is enclosed in hard or soft shell gelatin capsules, or it is compressed into tablets, or it is incorporated directly with the food of the diet. In some embodiments, the *cannabis* plant residue is incorporated with excipient and used in the form of ingestible tablets, buccal tablets, troches, capsules, caplets, pellets, granules, lozenges, chewing gum, powders, syrups, elixirs, wafers, aqueous solutions and suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). In embodiments, the tablets are coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions are formulated, for example as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In some embodiments, liposomes are formed from a variety of phospholipids, such as cholesterol, stearylamine or phosphatidylcholines. For oral administration in a capsule form, useful carriers or diluents include lactose and dried corn starch.

In some embodiments, liquid preparations for oral administration take the form of, for example, solutions, syrups or suspensions, or they are suitably presented as a dry product for constitution with water or other suitable vehicle before use. When aqueous suspensions and/or emulsions are administered orally, the *cannabis* plant residue of the disclosure is suitably suspended or dissolved in an oily phase that is combined with emulsifying and/or suspending agents. If desired, certain sweetening and/or flavoring and/or coloring agents are added. Such liquid preparations for oral administration are prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

Examples of excipients that can be used with the *cannabis* plant residue and compositions of the present disclosure include for example Methocel K-100-M™, Methodcel E-4-M™, leucine powder, silicified microcrystalline cellulose, calcium undecylenate, magnesium laurate, calcium laurate, silicone dioxide (e.g. AEROSIL 200 PHARMA, SIPERNAT 22™) powdered cellulose, citric acid, microcrystalline cellulose, medium chain triglyceride (MCT) oil, carboxymethylcellulose gum (e.g. Ticalose 6000™).

In another aspect, the present disclosure includes a prebiotic composition comprising a *cannabis* plant residue and hempseed hull, the composition having a cannabinoid content of about 5% or less than 5%. In some embodiments, the prebiotic composition of the present disclosure has a cannabinoid content of at most 5%.

In another aspect, the present disclosure includes a prebiotic of the present disclosure for use as a prebiotic dietary supplement.

In some embodiments, the *cannabis* plant residue is the *cannabis* plant residue of the present disclosure.

In some embodiments, the cannabinoid content is at most 3%, at most 1%, at most 0.5%, or at most 0.1%. In some embodiments, the cannabinoid content is about 3% or less than 3%, about 1% or less than 1%, about 0.5% or less than 0.5%, or about 0.1% or less than 0.1%.

In some embodiments, the hempseed hull is substantially free of cannabinoids, optionally, the hempseed hull comprising about 40 wt % to about 70 wt % of carbohydrate, about 50 wt % to about 70 wt % of carbohydrate, about 55 wt % to about 65 wt % of carbohydrate, or about 62%.

In some embodiments, the hempseed hull is untreated hempseed hull. In some embodiments, the hempseed hull is ground, pulverized and/or milled.

The hempseed hull can be obtained from for example hulling whole hempseeds using methods known in the art. For example, whole hempseeds can be inputted in a hopper, and de-hulled. After the de-hulling process, the hull and the hulled hempseeds can be separated. Further processing can be performed on the hempseed hull including but is not limited to pulverizing, grinding, milling, filtering, and/or being pressed into a cake.

The hempseed hull may be in the form of meal or powder, such as a meal or a powder suitable for formulation in dietary items or supplements.

In some embodiments, the prebiotic composition further comprises one or more of carrier, excipient, flavouring agent, or diluent.

In some embodiments, excipients can be added. For example, excipients can be added to the hempseed hull and/or to the prebiotic composition. The excipients may have functions including aid in suspension or dispersion, improving stability, preventing caking and/or modifying flavour.

It can be appreciated that the hempseed hull and the *cannabis* plant residue of the present disclosure may be combined by methods known in the art. For example, the hempseed hull and the *cannabis* plant residue of the present disclosure may be mixed, combined, or blended to homogenize the two ingredients such as to obtain a homogenous mixture. For example, the mixing, combining or blending can be carried with a ribbon blender, V blender, and or high-shear mixer. It can be appreciated that the choice of equipment may be based on volume of the material being blended, and or their chemical and physical properties.

It is envisioned that in preparing the prebiotic composition, the hempseed hull and the *cannabis* plant residue of the present disclosure may be combined first, prior to the addition of other components if present, such as excipients, carriers, flavouring agents, diluents, and/or preservatives. However, it is also envisioned that each of hempseed hull and the *cannabis* plant residue of the present disclosure may be individually mixed with one or more of the other components if present prior to being combined. Further, it is also envisioned that all components of the prebiotic composition may be combined at the same time.

In some embodiments, the composition comprises about 20% w/w to about 99% w/w hempseed hull and about 1% w/w to about 80% w/w *cannabis* plant residue. In some embodiments, the composition comprises about 40% to about 97% hempseed hull and about 3% w/w to about 60% w/w of the *cannabis* plant residue. In some embodiments, the composition comprises about 30% to about 60% hempseed hull and about 70% w/w to about 40% w/w *cannabis* plant residue. In some embodiments, the composition comprises about 40% w/w to about 55% w/w hempseed hull and about 45% w/w to about 60% w/w *cannabis* plant residue. In some embodiments, the composition comprises about 80% w/w to about 99% w/w of hempseed hull and about 1% w/w to about 20% w/w of the *cannabis* plant residue. In some embodiments, the composition comprises about 85% w/w to about 97% w/w of hempseed hull, and about 3% w/w to about 15% w/w of the *cannabis* plant residue. In some embodiments, the composition comprises about 90% w/w to about 97% w/w hempseed hull and about 3% w/w to about 10% w/w *cannabis* plant residue. In some embodiments, the composition comprises about 20% w/w to about 40% w/w of hempseed hull and about 80% w/w to about 60% w/w *cannabis* plant residue. In some embodiments, the composition comprises about 30% w/w to about 40% w/w of hempseed hull and about 70% w/w to about 60% w/w *cannabis* plant residue.

In some embodiments, the composition comprises about 30% w/w, about 35% w/w, about 40% w/w, about 45% w/w, about 50% w/w, about 55% w/w, or about 60% w/w of hempseed hull. In some embodiments, the composition comprises about 65% w/w, about 60% w/w, about 55% w/w, about 50% w/w, about 45% w/w, or about 40% w/w of the *cannabis* plant residue.

In some embodiments, the composition comprises about 80% w/w, about 85% w/w, about 90% w/w, about 95% w/w, or about 99% w/w of hempseed hull. In some embodiments, the composition comprises about 20% w/w, about 15% w/w, about 10% w/w, about 5% w/w, or about 1% w/w of the cannabis plant residue.

In some embodiments, the composition comprises about 94% w/w to about 96% w/w of hempseed hull and about 4% w/w to about 6% w/w of cannabis plant residue.

In some embodiments, the composition comprises about 20% w/w, about 25% w/w, about 30% w/w, about 35% w/w, or about 40% w/w of hempseed hull. In some embodiments, the composition comprises about 80% w/w, about 75% w/w, about 70% w/w, about 65% w/w, or about 60% w/w of the cannabis plant residue.

In some embodiments, the mass ratio of the cannabis plant residue to the hempseed hull is about 1:20 to about 1:10, about 1:18 to about 1:12, or about 1:16. In some embodiments, the mass ratio of the cannabis plant residue to the hempseed hull is about 20:1 to about 10:1, about 18:1 to about 12:1, or about 16:1. In some embodiments, the mass ratio of the cannabis plant residue to the hempseed hull is about 2:1 to about 1:2, about 1.5:1 to about 1:1.5, or about 1:1.

III. Methods and Uses of the Disclosure

In another aspect, the present disclosure includes a use of a cannabis plant residue of the present disclosure in the preparation of a prebiotic dietary supplement.

In another aspect, the present disclosure includes a use of a cannabis plant residue of the present disclosure as a prebiotic dietary supplement in a subject in need thereof.

In another aspect, the present disclosure includes a method of providing a prebiotic supplement to a subject in need thereof comprising administering to the subject an effective amount of a cannabis plant residue of the present disclosure.

In another aspect, the present disclosure includes a method of providing a prebiotic supplement to a subject in need thereof comprising administering to the subject an effective amount of prebiotic composition of the present disclosure.

In another aspect, the present disclosure includes a use of a prebiotic composition of the present disclosure in the preparation of a prebiotic dietary supplement.

In another aspect, the present disclosure includes a use of a prebiotic composition of the present disclosure as a prebiotic dietary supplement in a subject in need thereof.

In some embodiments, the cannabis plant residue is administered or used in a unit dose of about 0.1 g to about 1.5 g. In some embodiments, the cannabis plant residue is administered or used in the unit dose of about 0.3 g to about 1 g. In some embodiments, the cannabis plant residue is administered or used in the unit dose of about 0.5 g to about 0.7 g. In some embodiments, the cannabis plant residue is administered or used in the unit dose of about 0.5 g.

In some embodiments, the cannabis plant residue is administered or used 2 or 3 times per day. In some embodiments, the cannabis plant residue is administered or used 3 times per day.

In some embodiments, the cannabis plant residue is administered or used in an amount of about 0.5 g to about 50 g per day, about 1 g to about 40 g per day, or about 10 g to about 30 g per day. In some embodiments, the cannabis plant residue is administered or used in the amount of about 0.5 g to about 3 g per day. In some embodiments, the cannabis plant residue is administered or used in the amount of about 1.5 g to about 3 g per day. In some embodiments, the cannabis plant residue is administered or used in the amount of about 1.5 g per day. In some embodiments, the cannabis plant residue is administered or used in an amount of at least 1.5 g per day.

In some embodiments, the cannabis plant residue is administered or used in combination with a probiotic supplement, a parabiotic supplement, a postbiotic supplement, a second prebiotic supplement, and/or one or more cannabinoids.

In some embodiments, the prebiotic composition is administered or used in combination with a probiotic supplement, a parabiotic supplement, a postbiotic supplement, a second prebiotic supplement, and/or one or more cannabinoids.

In some embodiments, the second prebiotic supplement is selected from hempseed hull, fructans, galacto-oligosaccharides, starch and/or glucose-derived oligosaccharides, pectin oligosaccharides, non-carbohydrate oligosaccharides, and combinations thereof. In some embodiments, the second prebiotic is selected from hempseed hull, inulin, and combinations thereof. In some embodiments, the second prebiotic is the hempseed hull. In some embodiments, the hempseed hull is as described herein. In some embodiments, the second prebiotic supplement is inulin.

In some embodiments, the probiotic supplement is microorganisms selected from Lactobacillus species, Bifidobacterium species, Baccilus species, Streptococcus species, Enterococcus species, Saccharomyces species, and combinations thereof.

In some embodiments, the second prebiotic supplement is inulin, and the inulin is administered or used in a unit dose of about 1 g to about 3 g, about 1.5 g to about 2.5 g, or about 2 g. In some embodiments, the second prebiotic supplement is inulin, and the inulin is administered or used in an amount of about 2 g to about 10 g per day, about 5 g to about 8 g per day, about 6 g to about 7 g per day, or about 6 g per day.

In some embodiments, cannabis plant residue is administered or used orally.

In some embodiments, the cannabis plant residue is administered or used contemporaneously with, prior to or subsequent to food in-take.

In some embodiments, the cannabis plant residue is formulated in a tablet, a capsule, a powder or a soft chewable tablet.

In some embodiments, the cannabis plant residue is comprised in a dietary item.

In some embodiments, the prebiotic composition is administered or used in a unit dose of about 1 g to about 40 g, about 2 g to about 30 g, about 5 g to about 25 g, about 10 g to about 20 g, about 1 g to about 10 g, about 5 g to about 15 g, about 15 g to about 25 g, about 25 g to about 35 g, about 35 g to about 40 g, about 1 g, about 3 g, about 5 g, about 7 g, about 9 g, about 10 g, about 12 g, about 15 g, about 18 g, about 20 g, about 22 g, about 25 g, about 27 g, about 30 g, about 32 g, about 35 g, about 37 g, or about 40 g.

In some embodiments, the prebiotic composition is administered or used 1, 2 or 3 times per day.

In some embodiments, the prebiotic composition is administered or used in an amount of about 1 g to about 120 g per day, about 2 g to about 90 g per day, about 5 g to about 75 g per day, about 10 g to about 60 g per day, about 1 g to about 30 g per day, about 5 g to about 45 g per day, about 15 g to about 75 g per day, about 25 g to about 105 g per day, about 35 g to about 120 g per day, about 1 g per day, about 2 g per day, about 3 g per day, about 5 g per day, about 6 g per day, about 7 g per day, about 9 g per day, about 10 g per day, about 12 g per day, about 14 g per day, about 15 g per day, about 18 g per day, about 20 g per day, about 21 g per day, about 22 g per day, about 24 g per day, about 25 g per day, about 27 g per day, about 27 g per day, about 30 g per day, about 32 g per day, about 35 g per day, about 36 g per day, about 37 g per day, about 40 g per day, about 44 g per day, about 45 g per day, about 50 g per day, about 54 g per day, about 60 g per day, about 64 g per day, about 66 g per day, about 70 g per day, about 74 g per day, about 75 g per day, about 80 g per day, about 81 g per day, about 90 g per day, about 96 g per day, about 105 g per day, about 111 g per day, about 120 g per day.

In some embodiments, the prebiotic composition is administered or used orally.

In some embodiments, the prebiotic composition is administered or used contemporaneously with, prior to, or subsequent to food intake.

In some embodiments, the prebiotic composition is formulated in a tablet, a capsule, a powder or a soft chewable tablet.

In some embodiments, the prebiotic composition is formulated in a dietary item.

In some embodiments, the dietary item is selected from a smoothie, a salad-dressing, a beverage, a protein bar, a chocolate bar, a meal replacement, a powder-form seasoning, a liquid-form seasoning, a spreadable condiment, a powder-form beverage mix, a cereal, a bread, a yogurt, a fermented food, and a pasta.

The dosage of a *cannabis* plant residue or the prebiotic composition of the disclosure varies depending on many factors such as the pharmacodynamic properties of the *cannabis* plant residue, the mode of administration, the age, health and weight of the recipient, the nature and extent of the symptoms, the frequency of the treatment and the type of concurrent treatment, if any, and the clearance rate of the *cannabis* plant residue in the subject to be treated.

EXAMPLES

The following non-limiting examples are illustrative of the present disclosure.

Example 1 Illustrative Example of Preparation of *Cannabis* Plant Residue

The *cannabis* plant residue of the present disclosure can be prepared for example according to the following general process. It is appreciated by a person skilled in the art that some aspects of the general process can be adjusted and modified without affecting the resulting *cannabis* plant residue.

Dried *Cannabis sativa* plant parts (e.g. flower, sugar leaves, and stems) were milled by a grinder. Confirmatory identification (botanical plant identification of *Cannabis sativa*) was performed on the milled, dried product using an NIR Multipurpose Analyzer. The milled plant parts were subjected to decarboxylation to convert acidic forms of cannabinoids.

The decarboxylated plant parts were extracted using super critical $CO_2$ extraction with a Waters Bio-Botanical™ Extraction System (BBES). For example, the super critical $CO_2$ extraction can be conducted at about 30° C. to about 90° C., and at a pressure of around 1500 PSI to 5000 PSI. The *cannabis* oil extracted from the plant parts contains the majority of cannabinoids and can be used for other purposes.

The residual plant material forms the *cannabis* plant residue. Optionally, the residual plant material from the super critical $CO_2$ extraction can be subjected to a secondary extraction by for example ethanol/$CO_2$ extraction. The *cannabis* plant residue thus prepared was analysed for its cannabinoid content. The results are shown in Table 1.

TABLE 1

| Cannabinoid Level Analysis | | | | | |
| --- | --- | --- | --- | --- | --- |
| | | | Value (% w/w) | | |
| Cannabis Plant Residue Analytes | Lower Limit | Reporting Limit | Lab Recorded Values | Post Extract Upper Limit | Supple-mental Upper Limit |
| Delta 9-Tetrahydrocannabinol (Delta 9-THC) | 0 | 0.05 | <0.05 | 0.05 | 1.1 |
| Delta 9-Tetrahydrocannabinolic Acid (Delta 9-THCA) | 0 | 0.05 | <0.05 | 0.05 | 1.1 |
| Cannabidiol (CBD) | 0 | 0.05 | 0.16 | 0.3 | 3.1 |
| Cannabidiolic Acid (CBDA) | 0 | 0.05 | 0.79 | 0.9 | 2.1 |
| Cannabigerol (CBG) | 0 | 0.05 | <0.05 | 0.05 | 1.1 |
| Cannabigerolic Acid (CBGA) | 0 | 0.05 | 0.09 | 0.2 | 1.1 |
| Cannabinol (CBN) | 0 | 0.05 | <0.05 | 0.05 | 1.1 |
| Cannabichromene (CBC) | 0 | 0.05 | <0.05 | 0.05 | 1.1 |
| Total Delta 9-Tetrahydrocannabinol (Delta 9-THC) | 0 | 0.07 | <0.07 | 0.07 | 1.1 |
| Total Cannabidiol (CBD) | 0 | 0.07 | 0.85 | 1 | 2.1 |
| Total Cannabigerol (CBG) | 0 | 0.07 | 0.08 | 0.2 | 1.1 |

Example 2 Proximate Analysis of *Cannabis* Plant Residue

A sample of the *cannabis* plant residue prepared according to Example 1 was characterized by proximate analysis for its fiber, carbohydrate, protein, and hydration contents. The results are shown in Table 2. The *cannabis* plant residue contains a high level of dietary fiber. Further, the majority of the dietary fiber was shown to be insoluble dietary fiber.

TABLE 2

| Proximate analysis of cannabis plant residue | |
| --- | --- |
| Hydration properties | |
| Water Hydration Capacity (WHC g/g) | 6.43 ± 0.22 |
| Water Solubility Index (WSI %) | 0.08 ± 0.004 |
| Dietary fiber analysis (%) | |
| Total Dietary Fiber | 69.24 |
| Insoluble Dietary Fiber | 65.58 |
| Soluble Dietary Fiber | 3.73 |
| Proximate analysis | |
| Total Carbohydrate (% w/w) | 2.39 ± 0.12 |
| Soluble Protein (mg/g) | 3.7 ± 0.01 |
| Crude Protein (% w/w) | 18.1 |

Example 3 Effect of *Cannabis* Plant Residue on Growth of Intestinal Microorganisms General Methodology Inulin from dahlia tubers was obtained from Sigma-Aldrich. Growth media was prepared according to Tzounis et al. (British Journal of Nutrition, 2008, 99:782-7922008) using 2 g/L proteose peptone, 2 g/L yeast extract, 0.1 g/L NaCl, 0.04 g/L $K_2HPO_4$, 0.04 g/L $KH_2PO_4$, 2 g/L $NaHCO_3$, 0.01 g/L $MgSO_4\cdot7H_2O$, 0.01 g/L $CaCl_2\cdot6H_2O$, 2 mL/L Tween 80, 0.05 g/L Hemin, 10 μL/L MEM vitamin solution, 0.5 g/L L-cysteine, 0.5 g/L bile salts, 0.001 g/L resazurin and autoclaved $dH_2O$.

Batch Fermentation

Simulation of GI conditions was done using a dynamic computer-controlled model that utilizes several 250 mL independent fermentation vessels run in parallel. All vessels were maintained under anaerobic conditions by purging with oxygen-free nitrogen gas. Vessel contents were continuously stirred using magnetic stirrers and maintained at 37° C. using heated double-jacketed beakers. The pH monitoring and regulation of each vessel during enzymatic digestion and fermentation was done using python coding of a Raspberri Pi™ microprocessor (ver. 1B) with an embedded EZO™ pH circuit (Altas Scientific, NY, USA). Addition of 0.5 M NaOH or 0.5 M HCl was carried out to maintain pH using computer-controlled peristaltic pumps (Gaisawat et al., *Nutrients.*, 2019, 11(9). pii: E2007. doi: 10.3390/nu11092007).

In vitro digestion was adapted from Miranda et al. (*Food and Function,* 2013, 4, 1595-1601). Vessels contained either inulin (control) or *cannabis* plant residue as prepared in Example 1. One gram of each treatment was added to their respective autoclaved vessel along with 100 mL of phosphate buffered saline. To each vessel, 2 mL of amylase (707.83 mg α-amylase/1.5 mL water) were added and the pH was manually adjusted to 7 (±0.2), using NaOH (0.5 M or 0.1 M), and incubated for 15 minutes, to simulate oral digestion. Gastric digestion was then initiated by adjusting the pH to 2 (±0.2) and adding 2 mL pepsin (1.167 g pepsin/1.5 mL) and incubating for 90 minutes. The pH was then raised to 8 (±0.2) and 30 mL of pancreatic juice (12 g/L of $NaHCO_3$, 6 g/L of bile extracts/salts, 0.9 g/L of pancreatin were added, and the vessels incubated for 120 minutes to simulate small intestinal digestion.

Stock solutions of *Lactobacillus rhamnosus* GG or *Bifidobacterium longum* BB536® (LifeExtension®) were prepared in autoclaved saline and used to inoculate each vessel (1 mL), along with 50 mL of growth medium at 37° C., for a final concentration of 108 CFU/vessel. Time 0 indicates the addition of the bacterial solution and growth medium. Five mL Samples were withdrawn from each vessel at times 0, 8, and 12 h for microbial growth assessment. Three independent experiments were conducted.

Microbial Growth Assessment

Bacterial growth was monitored via OD measurements at 600 nm using a spectrophotometer. Bacterial suspensions were mixed by vortexing for 10 seconds prior to measurement and assessed in duplicate. Values were converted into fold-change from values at time 0 and combined with fold-change values obtained in the first round of fermentations performed in March-April 2018, for a total of 5 independent experiments. Results were analyzed via two-way ANOVA using JMP 14.1.0 (SAS Institute Inc.). A p-value <0.05 was considered significant.

Figure 2:
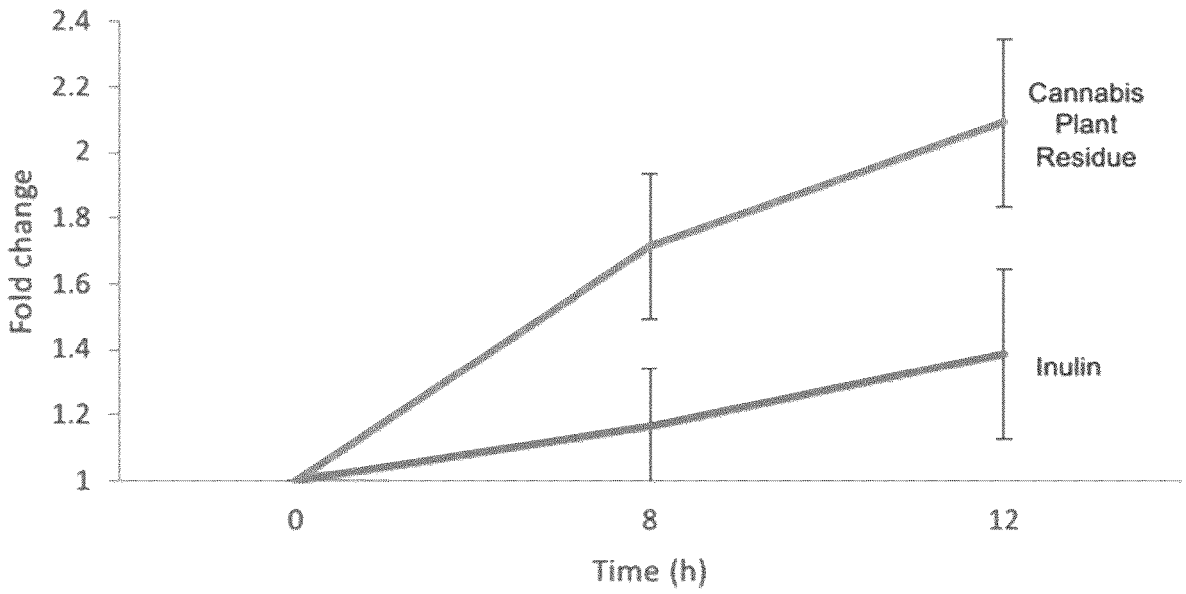
FIG. 2 shows the growth curve of *Bifidobacterium longum* when treated with inulin (control), or *cannabis* plant residue as assessed by OD measurements at 600 nm at 0, 8, and 12 h of fermentation.
Figure 3:
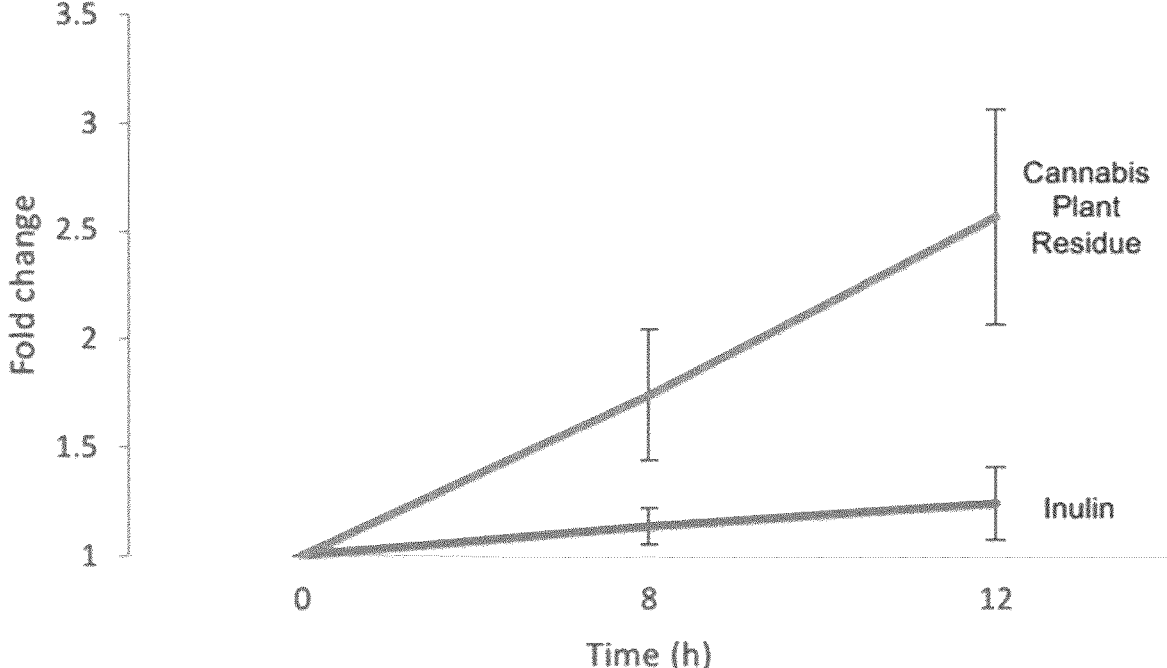
FIG. 3 shows the growth curve of *Lactobacillus rhamnosus* when treated with inulin (control), or *cannabis* plant residue as assessed by OD measurements at 600 nm at 0, 8, and 12 h of fermentation.

The growth curves of the intestinal microorganisms used are shown in FIG. 2 for *L. rhamnosus* and in FIG. 3 for *B.*

*longum.* The resulting data of in-vitro gastrointestinal simulation modeling showed a statistically significant increase in growth in cultures treated with the *cannabis* plant residue in comparison to Inulin. This demonstrates that the *cannabis* plant residue can be used as an effective prebiotic.

Example 4 Prebiotic Composition of *Cannabis* Plant Residue and Hempseed Hull

The hempseed hull used for some embodiments of the compositions of the present disclosure was analyzed for its compositional properties, which are shown in Tables 3 to 7.

Ash content was measured using Official Methods of Analysis of AOAC INTERNATIONAL, 18th Ed., Method 923.03, AOAC INTERNATIONAL, Gaithersburg, MD, USA, (2005). (Modified)

Bromide content was measured using methods reported in:

Community Reference Laboratory for Single Residue Methods, CVUA, Stuttgart, Schaglandstr 3/2, 70736 Fellbach, Germany T. Stijve, Gas Chromatographic Determination of Inorganic Bromide Residues—a Simplified Procedure, Dtsch. Lebenm Rundsch 77 99-101 (1981).

Deutsche Forschungsgeneinschaft (DFG), Manual of Pesticide Residue Analysis, Volume I by Verlag Chemie, 1987 ISBN 3-527-27010-8.

Carbohydrate content was measured using methods in United States Department of Agriculture, "Energy Value of Foods", Agriculture Handbook No. 74, pp. 2-11, (1973).

Fat by acid hydrolysis was measured using methods reported in:

Food Products that are not Dairy, Egg or Cheese Products: Official Methods of Analysis of AOAC INTERNATIONAL (2005) 18TH Ed., AOAC, INTERNATIONAL, Gaithersburg, MD, USA, Official Methods 922.06 and 954.02. (Modified)

Cheese and Cheese Products: Official Methods of Analysis of AOAC INTERNATIONAL (2005) 18th Ed., AOAC INTERNATIONAL, Gaithersburg, MD, USA, Official Method 933.05. (Modified)

Egg, Egg Products, and Mayonnaise: Official Methods of Analysis of AOAC INTERNATIONAL (2005) 18th Ed., AOAC INTERNATIONAL, Gaithersburg, MD, USA, Official Method 925.32. (Modified).

Moisture content was measured using M100_T100 (M100T100_S) Official Methods of Analysis of AOAC INTERNATIONAL, 18th Ed., Methods 925.09 and 926.08, AOAC INTERNATIONAL, Gaithersburg, MD, USA, (2005). (Modified).

Protein (N×6.25) content was measured using the Dumas method (DGEN_S) Official Methods of Analysis of AOAC INTERNATIONAL, 18th Ed., Methods 968.06 and 992.15, AOAC INTERNATIONAL, Gaithersburg, MD, USA, (2005). (Modified).

Total Content of Dithiocarbamates (DTCs) expressed as CS2 per USP <561> (DTC_PKG) was measured using methods reported in Hayama, T. and Takada, M., "Simple and Rapid method for the determination of Ethylenebisdithiocarbamate Fungicides in Fruits and Vegetables Using Liquid Chromatography with Tandem Mass Spectrometry," Anal. Bioanal. Chem., 392:969-976 (2008).

Total dietary fiber content was measured using Official Methods of Analysis of AOAC INTERNATIONAL 18th Ed., Method 991.43, AOAC INTERNATIONAL, Gaithersburg, MD, USA, (2005). (Modified).

USP pesticides contents were measured using methods below:

Official Methods of Analysis, AOAC Official Method 2007.01, Pesticide Residues in Foods by Acetonitrile Extraction and Partitioning with Magnesium Sulfate, AOAC INTERNATIONAL (modified).

CEN Standard Method EN 15662: Food of plant origin—Determination of pesticide residues using GC-MS and/or LC-MS/MS following acetonitrile extraction/partitioning and clean-up by dispersive SPE—QuEChERS method.

EP Chapter 2.8.13 Pesticide Residues, The European Pharmacopoeia

USP Chapter <561> Articles of Botanical Origin, The United States Pharmacopeia.

TABLE 3

Compositional Analysis of Hempseed Hull

| Analysis | Result |
|---|---|
| Fat by Acid Hydrolysis | |
| Fat | 12.6% |
| Carbohydrates | |
| Total Carbohydrates | 61.6% |
| Total Dietary Fiber | |
| Total Dietary Fiber | 62.0% |
| Protein (N × 6.25) Dumas Method | |
| Protein | 13.2% |
| Ash | |
| Ash | 3.09% |
| Moisture by M100_T100 | |
| Moisture | 9.39% |

TABLE 4

Compositional Analysis of Hempseed Hull

| Analysis | Limit | Result | Pass/Fail |
|---|---|---|---|
| Bromide per USP <561> | | | |
| Bromide, inorganic (calculated as Bromide Ion) | 125 mg/kg | <125 mg/kg | Pass |
| Total Content of Dithiocarbamates (DTCs) expressed as CS2 per USP <561> | | | |
| Total Content of Dithiocarbamates (DTCs) expressed as CS2 | 2 mg/kg | <2 mg/kg | Pass |
| USP <561> Pesticides | | | |
| Acephate | 0.1 mg/kg | <0.1 mg/kg | Pass |
| Alachlor | 0.05 mg/kg | <0.05 mg/kg | Pass |
| Aldrin and dieldrin (sum of) | 0.05 mg/kg | <0.05 mg/kg | Pass |
| Azinphos-ethyl | 0.1 mg/kg | <0.1 mg/kg | Pass |
| Azinphos-methyl | 1 mg/kg | <1 mg/kg | Pass |
| Bromophos-ethyl | 0.05 mg/kg | <0.05 mg/kg | Pass |
| Bromophos-methyl | 0.05 mg/kg | <0.05 mg/kg | Pass |

TABLE 4-continued

Compositional Analysis of Hempseed Hull

| Analysis | Limit | Result | Pass/Fail |
|---|---|---|---|
| Bromopropylate | 3 mg/kg | <3 mg/kg | Pass |
| Chlordane (sum of cis- and trans- isomers and oxychlordane) | 0.05 mg/kg | <0.05 mg/kg | Pass |
| Chlorfenvinphos | 0.5 mg/kg | <0.5 mg/kg | Pass |

TABLE 5

Compositional Analysis of Hempseed Hull

| Analysis | Limit | Result | Pass/Fail |
|---|---|---|---|
| USP <561> Pesticides | | | |
| Chlorpyrifos-ethyl | 0.2 mg/kg | <0.2 mg/kg | Pass |
| Chlorpyrifos-methyl | 0.1 mg/kg | <0.1 mg/kg | Pass |
| Chlorthal-dimethyl | 0.01 mg/kg | <0.01 mg/kg | Pass |
| Cyfluthrin (sum of isomers) | 0.1 mg/kg | <0.1 mg/kg | Pass |
| Cyhalothrin, lambda- | 1 mg/kg | <1 mg/kg | Pass |
| Cypermethrin (sum of isomers) | 1 mg/kg | <1 mg/kg | Pass |
| DDT (sum of o,p'-DDT, p,p'-DDT, o,p'-DDE, p,p'-DDE, o,p'-DDD, and p,p'-DDD) | 1 mg/kg | <1 mg/kg | Pass |
| Deltamethrin | 0.5 mg/kg | <0.5 mg/kg | Pass |
| Diazinon | 0.5 mg/kg | <0.5 mg/kg | Pass |
| Dichlofluanid | 0.1 mg/kg | <0.1 mg/kg | Pass |
| Dichlorvos | 1 mg/kg | <1 mg/kg | Pass |
| Dicofol | 0.5 mg/kg | <0.5 mg/kg | Pass |
| Dimethoate and omethoate (sum of) | 0.1 mg/kg | <0.1 mg/kg | Pass |
| Endosulfan (sum of isomers and endosulfan sulfate) | 3 mg/kg | <3 mg/kg | Pass |
| Endrin | 0.05 mg/kg | <0.05 mg/kg | Pass |
| Ethion | 2 mg/kg | <2 mg/kg | Pass |
| Etrimphos | 0.05 mg/kg | <0.05 mg/kg | Pass |
| Fenchlorphos (sum of fenchlorphos and fenchlorphos-oxon) | 0.1 mg/kg | <0.1 mg/kg | Pass |

TABLE 5-continued

Compositional Analysis of Hempseed Hull

| Analysis | Limit | Result | Pass/Fail |
|---|---|---|---|
| Fenitrothion | 0.5 mg/kg | <0.5 mg/kg | Pass |
| Fenpropathrin | 0.03 mg/kg | <0.03 mg/kg | Pass |
| Fensulfothion (sum of fensulfothion, fensulfothion-oxon, fensulfothion-oxon sulfone and fensulfothion sulfone) | 0.05 mg/kg | <0.05 mg/kg | Pass |
| Fenthion (sum of fenthion, fenthion-oxon, fenthion-oxon sulfone, fenthion-oxon sulfoxide, fenthion sulfone and fenthion sulfoxide) | 0.05 mg/kg | <0.05 mg/kg | Pass |
| Fenvalerate | 1.5 mg/kg | <1.5 mg/kg | Pass |
| Flucythrinate | 0.05 mg/kg | <0.05 mg/kg | Pass |

TABLE 6

Compositional Analysis of Hempseed Hull

| Analysis | Limit | Result | Pass/Fail |
|---|---|---|---|
| USP <561> Pesticides | | | |
| Fluvalinate, tau- | 0.05 mg/kg | <0.05 mg/kg | Pass |
| Fonofos | 0.05 mg/kg | <0.05 mg/kg | Pass |
| Heptachlor (sum of heptachlor and cis- and trans-heptachlor epoxides) | 0.05 mg/kg | <0.05 mg/kg | Pass |
| Hexachloro-benzene | 0.1 mg/kg | <0.1 mg/kg | Pass |
| Hexachloro-cyclohexane isomers (other than gamma) | 0.3 mg/kg | <0.3 mg/kg | Pass |
| Lindane (gamma-hexachlorocyclohexane) | 0.6 mg/kg | <0.6 mg/kg | Pass |
| Malathion and malaoxon (sum of) | 1 mg/kg | <1 mg/kg | Pass |
| Mecarbam | 0.05 mg/kg | <0.05 mg/kg | Pass |
| Methacriphos | 0.05 mg/kg | <0.05 mg/kg | Pass |
| Meth-amidophos | 0.05 mg/kg | <0.05 mg/kg | Pass |
| Methidathion | 0.2 mg/kg | <0.2 mg/kg | Pass |
| Methoxychlor | 0.05 mg/kg | <0.05 mg/kg | Pass |
| Mirex | 0.01 mg/kg | <0.01 mg/kg | Pass |
| Mono-crotophas | 0.1 mg/kg | <0.1 mg/kg | Pass |

TABLE 6-continued

Compositional Analysis of Hempseed Hull

| Analysis | Limit | Result | Pass/Fail |
|---|---|---|---|
| Parathion-ethyl and paraoxon-ethyl (sum of) | 0.5 mg/kg | <0.5 mg/kg | Pass |
| Parathion-methyl and paraoxon-methyl (sum of) | 0.2 mg/kg | <0.2 mg/kg | Pass |
| Pendimethalin | 0.1 mg/kg | <0.1 mg/kg | Pass |
| Penta-chloranisol | 0.01 mg/kg | <0.01 mg/kg | Pass |
| Permethrin (sum of isomers) | 1 mg/kg | <1 mg/kg | Pass |
| Phosalone | 0.1 mg/kg | <0.1 mg/kg | Pass |
| Phosmet | 0.05 mg/kg | <0.05 mg/kg | Pass |
| Piperonyl butoxide | 3 mg/kg | <3 mg/kg | Pass |
| Pirimiphos-ethyl | 0.05 mg/kg | <0.05 mg/kg | Pass |
| Pirimiphos-methyl (sum of pirimiphos-methyl and N-desethyl-pirimiphos-methyl) | 4 mg/kg | <4 mg/kg | Pass |
| Procymidone | 0.1 mg/kg | <0.1 mg/kg | Pass |
| Profenophos | 0.1 mg/kg | <0.1 mg/kg | Pass |
| Prothiophos | 0.05 mg/kg | <0.05 mg/kg | Pass |

TABLE 7

Compositional Analysis of Hempseed Hull

| Analysis | Limit | Result | Pass/Fail |
|---|---|---|---|
| USP <561> Pesticides | | | |
| Pyrethrum (sum of cinerin I, cinerin II, jasmolin I, jasmolin II, pyrethrin I, and pyrethrin II) | 3 mg/kg | <3 mg/kg | Pass |
| Quinalphos | 0.05 mg/kg | <0.05 mg/kg | Pass |
| Quintozene (sum of quintozene, pentachloro-aniline and methyl pentachloro-phenyl sulfide) | 1 mg/kg | <1 mg/kg | Pass |
| S-421 | 0.02 mg/kg | <0.02 mg/kg | Pass |
| Tecnazene | 0.05 mg/kg | <0.05 mg/kg | Pass |
| Tetradifon | 0.3 mg/kg | <0.3 mg/kg | Pass |
| Vinclozolin | 0.4 mg/kg | <0.4 mg/kg | Pass |

The hempseed hull was also analyzed for its cannabinoid content by HPLC. Various cannabinoids have been assessed, the results of which are shown in Table 8.

The chromatographic conditions are shown below:

Method: ATM-815-0300

Column: AP270 Kinetex 2.6 μm C18 100A (150×4.6 mm)

Temperature: 30° C.

Flow rate: 1 mL/min

Injection volume: 5 μL

UV detection: 228 nm

Mobile phase: 0.1% formic acid in water; 0.1% Formic acid in methanol:acetonitrile (75:25)

Instrument: Alliance™_1

Sample preparation: Transferred approximately 125 mg of sample to a 25 mL volumetric flask and filled to volume with methanol. Vortexed 30 seconds and sonicated 15 minutes at room temperature. Filtered through 0.2 pm syringe filter. Transferred into HPLC vial for analysis.

Cannabinoids were not detected in the hempseed hull sample.

TABLE 11

| Microbiological Testing Data of Hempseed Hull | | | |
|---|---|---|---|
| Microbiological Test | Specifications | Results | SOP# |
| Total Viable Count | <10,000 cfu/g | 141,400 cfu/g | 00103 |
| Yeast & Mold | <100 cfu/g | 5,600 cfu/g | 00088 |
| Coliform | <100 cfu/g | *ND@10 cfu/g | 00097 |
| E. coli | Absent in 10 g | Absent in 10 g | 00100 |
| Salmonella | Absent in 10 g | Absent in 10 g | 00078 |
| S. aureus | Absent in 10 g | Absent in 10 g | 00099 |

TABLE 8

| Cannabinoid Content of Hempseed Hull | | | | | | |
|---|---|---|---|---|---|---|
| Ret. Time (min) Compound Name | Prep 1 (%) | Prep 2 (%) | Average (%) | Average Dried Basis (%) | Specification | Result |
| 3.4 Cannabidivarin (CBDV) | ND | ND | ND | ND | Report Only | N/A |
| 4.1 Cannabidivarinic Acid (CBDVA) | ND | ND | ND | ND | Report Only | N/A |
| 5.5 Cannabidiol (CBD) | ND | ND | ND | ND | Report Only | N/A |
| 5.6 Cannabigerol (CBG) | ND | ND | ND | ND | Report Only | N/A |
| 6.2 Tetrahydrocannabidivarin (THCV) | ND | ND | ND | ND | Report Only | N/A |
| 6.8 Cannabidiolic Acid (CBDA) | ND | ND | ND | ND | Report Only | N/A |
| 9.5 Cannabigerolic Acid (CBGA) | ND | ND | ND | ND | Report Only | N/A |
| 9.8 Cannabinol (CBN) | ND | ND | ND | ND | Report Only | N/A |
| 11.0 $\Delta^9$-Tetrahydrocannabinol ($\Delta^9$-THC) | ND | ND | ND | ND | Report Only | N/A |
| 11.5 $\Delta^8$-Tetrahydrocannabinol ($\Delta^4$-THC) | ND | ND | ND | ND | Report Only | N/A |
| 13.2 Cannabichromene (CBC) | ND | ND | ND | ND | Report Only | N/A |
| 14.8 $\Delta^9$-Tetrahydrocannabinolic Acid A (THCA-A) | ND | ND | ND | ND | Report Only | N/A |
| Total THC ($\Delta^9$-THC + 0.877 THCA-A) | ND | ND | ND | ND | Report Only | N/A |
| Total cannabinoids | ND | ND | ND | ND | Report Only | N/A |

The hempseed hull was also analyzed for its mycotoxin content, the results of which are shown in Table 9.

TABLE 9

| Mycotoxin Content in Hempseed Hull | | |
|---|---|---|
| Analysis Performed | Specification | Result |
| Aflatoxin B1 | <2ppb | Negative |
| Total Aflatoxins | <4ppb | Negative |

The hempseed hull was also analyzed for its heavy metal content by inductively coupled plasma (ICP) mass spectrometry, the results of which are shown in Table 10.

TABLE 10

| Hempseed Hull ICP Analysis | | | | |
|---|---|---|---|---|
| Element | Date Tested | Result (ng/g = ppb) | Analysis (ug/g = ppm) | Spec (pm) |
| As | 11/30/20 | 16.8087 | 0.0 | <1.5 ppm |
| Cd | 11/30/20 | 30.3140 | 0.0 | <0.5 ppm |
| Pb | 11/30/20 | 15.2240 | 0.0 | ≤0.6 ppm |
| Hg | 11/30/20 | 3.2473 | 0.0 | ≤1.5 ppm |

The hempseed hull was also analyzed for microbiological content, the results of which are shown in Table 11.

As shown above, the hempseed hull of the present disclosure has a high carbohydrate content of over 60%. A significant portion of the carbohydrate content of the hempseed hull is present in polysaccharide forms such as xylan and pectin. As such, it can be appreciated that the hempseed hull of the present disclosure can be used as a source of prebiotic, for example in combination with the *cannabis* plant residue of the present disclosure.

For example, the hempseed hull can be combined with the *cannabis* plant residue of the present disclosure in a mass ratio of about 20:1 to about 10:1, about 18:1 to 12:1, or about 16:1. It can be expected that given the prebiotic activity of the *cannabis* plant residue of the present disclosure as shown herein and the high carbohydrate content of the hempseed hull of the present disclosure, the resulting composition would be useful as a prebiotic supplement.

While the present disclosure has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

The invention claimed is:

1. A method of providing a prebiotic supplement to a subject in need thereof comprising administering to the subject an effective amount of a seedless *cannabis* plant residue, the *cannabis* plant residue having a cannabinoid content of at most 5%.

2. The method of claim 1, wherein the *cannabis* plant residue is substantially free of cannabinoid.

3. The method of claim 1, wherein the *cannabis* plant residue is obtained by a treatment process comprising removing cannabinoids from a *cannabis* plant.

4. The method of claim 1, wherein the *cannabis* plant residue comprises about 15% w/w to about 85% w/w of total dietary fiber.

5. The method of claim 1, wherein the *cannabis* plant residue comprises about 10% w/w to about 80% w/w of insoluble dietary fiber.

6. The method of claim 1, wherein the *cannabis* plant residue comprises about 0.5% w/w to about 60% w/w of carbohydrate.

7. The method of claim 1, wherein the *cannabis* plant residue comprises about 10% w/w to about 30% w/w of protein.

8. The method of claim 1, wherein the *cannabis* plant residue is administered in combination with a probiotic supplement, a parabiotic supplement, a postbiotic supplement, a second prebiotic supplement, and/or one or more cannabinoids.

9. The method of claim 8, wherein the second prebiotic supplement is selected from hempseed hull, fructans, galacto-oligosacharides, starch, glucose-derived oligosaccharides, pectin oligosaccharides, non-carbohydrate olligosaccharides and combinations thereof.

10. The method of claim 8, wherein the probiotic supplement is microorganisms selected from *Lactobacillus* species, *Bifidobacterium* species, *Bacillus* species, *Streptococcus* species, *Enterococcus* species, *Saccharomyces* species, and combinations thereof.

11. The method of claim 1, wherein the *cannabis* plant residue is obtained by a treatment process, the treatment process comprising removing cannabinoids from a *cannabis* plant by super critical $CO_2$ extraction, by ethanol extraction, by $CO_2$ extraction, and/or by ethanol/$CO_2$ extraction.

12. The method of claim 1, wherein the *cannabis* plant residue is obtained from one or more above-ground *cannabis* plant part.

13. The method of claim 12, wherein the above-ground *cannabis* plant part consists of one or more of a flower, a sugar leaf, and/or a stem.

14. A prebiotic composition comprising a seedless *cannabis* plant residue and hempseed hull, the composition having a cannabinoid content of about 5% or less than 5%.

15. The prebiotic composition of claim 14, wherein the cannabinoid content is about 3% or less than 3%, about 1% or less than 1%, about 0.5% or less than 0.5%, or about 0.1% or less than 0.1%.

16. The prebiotic composition of claim 14, wherein the hempseed hull is substantially free of cannabinoids, optionally, the hempseed hull comprising about 40 wt % to about 70 wt % of carbohydrate, about 50 wt % to about 70 wt % of carbohydrate, about 55 wt % to about 65 wt % of carbohydrate, or about 62%.

17. The prebiotic composition of claim 14, wherein the composition comprises about 20% w/w to about 99% w/w hempseed hull and about 1% w/w to about 80% w/w *cannabis* plant residue.

18. Method of providing a prebiotic supplement to a subject in need thereof comprising administering to the subject an effective amount of a prebiotic composition as defined in claim 14.

19. The method of claim 18, wherein the prebiotic composition is administered in combination with a probiotic supplement, a parabiotic supplement, a postbiotic supplement, a second prebiotic supplement, and/or one or more cannabinoids.

20. The method of claim 19, wherein the second prebiotic supplement is selected from fructans, galacto-oligosacharides, starch, glucose-derived oligosaccharides, pectin oligosaccharides, non-carbohydrate oligosaccharides and combinations thereof.

21. The method of claim 20, where in the second prebiotic supplement is inulin.

22. The method of claim 19, wherein the probiotic supplement is microorganisms selected from *Lactobacillus* species, *Bifidobacterium* species, *Bacillus* species, *Streptococcus* species, *Enterococcus* species, *Saccharomyces* species, and combinations thereof.

23. A prebiotic composition comprising a *cannabis* plant residue and hempseed hull, the composition having a cannabinoid content of about 5% or less than 5%, wherein the mass ratio of the *cannabis* plant residue to the hempseed hull is about 1:20 to about 1:10, about 1:18 to about 1:12, or about 1:16.

* * * * *